United States Patent [19]
Yokoyama et al.

[11] Patent Number: 5,569,919
[45] Date of Patent: Oct. 29, 1996

[54] X-RAY ANALYTICAL APPARATUS

[75] Inventors: Kazushi Yokoyama; Norio Suzuki; Kenichi Inoue; Yukito Furukawa, all of Kobe, Japan

[73] Assignee: Kabushiki Kaisha Kobe Seiko Sho, Kobe, Japan

[21] Appl. No.: 530,408

[22] Filed: Sep. 19, 1995

[30] Foreign Application Priority Data

Oct. 4, 1994 [JP] Japan .................................. 6-239842

[51] Int. Cl.$^6$ ..................................................... H01K 49/08
[52] U.S. Cl. .............................................. 250/309; 378/84
[58] Field of Search .................................. 250/309, 305, 250/310, 306; 378/49, 81, 83, 84

[56] References Cited

U.S. PATENT DOCUMENTS

| | | | |
|---|---|---|---|
| 3,914,605 | 10/1975 | Hara | 378/83 |
| 4,680,467 | 7/1987 | Bryson, III et al. | 250/309 |

FOREIGN PATENT DOCUMENTS

| | | | |
|---|---|---|---|
| 0090847 | 7/1980 | Japan | 378/84 |
| 6258497 | 9/1994 | Japan | 378/84 |
| 681358 | 8/1979 | U.S.S.R. | 378/84 |

*Primary Examiner*—Jack I. Berman
*Assistant Examiner*—Kiet T. Nguyen
*Attorney, Agent, or Firm*—Oblon, Spivak, McClelland, Maier & Neustadt, P.C.

[57] ABSTRACT

An X-ray analytical apparatus of a wavelength dispersion type having a construction of essential parts improved using a microprobe of ion beam. An ion beam 10 is controlled to be deflected to scan in a fine region of a sample 3, a characteristic X-ray generated by irradiation of the ion beam is subjected spectro-process by a analyzing element 5 set to a predetermined radius of curvature by a curvature changing mechanism, and an X-ray having a specific wavelength selected by the spectro-process is detected by a proportional counter 7. When an angle of the analyzing element is set by a rotational stage to an incident angle of a specific X-ray determined by a detection element on the sample 3, a wide range of wavelength can be subjected to spectro-measured while the sample 3, the analyzing element 5 and the proportional counter 7 remain fixed in position. Since the proportional counter 7 is provided with a lengthy sensing portion, even if an incident position of the X-ray is changed, measurement can be made while a position of a detector remains fixed. Being a position sensitive type detector, incident position information of the X-ray different according to the wavelength can be removed, and the wavelength and strength of the X-ray can be measured while discriminating each X-ray quantum.

4 Claims, 7 Drawing Sheets

O-Kα RESULTS OF SPECTRO-EXPERIMENTS

X-RAY ANALYTICAL APPARATUS

BACKGROUND OF THE INVENTION

1. Field of the Invention

The present invention relates to an X-ray analytical apparatus for making the material evaluation, construction analysis and so forth of semiconductor materials or the like, and more specifically to an X-ray analytical apparatus of a wavelength dispersion type for the spectro-chemical analysis of characteristic X-rays generated from a sample using a high energy ion beam as a probe.

2. Description of the Related Art

As one of procedures for the construction analysis of materials at a atom level, an X-ray analytical apparatus using a curved analyzing crystal as schematically shown in FIG. 5 has been known. An analytical point of a sample 33, a analyzing crystal 34 and an X-ray detector (correctly, a detector slit) are arranged on a Rowland circle, and a characteristic X-ray generated when an electron beam, an ion beam or the like as a probe is irradiated on the analytical point of the sample 33 is subjected to spectro-process and condensation by the analyzing crystal 34 and detected by the X-ray detector 35.

In the above-described construction, the relative position between the sample and the analyzing crystal 34 and the direction thereof are varied with the spectral wavelength. As shown in FIG. 6, the position of the sample 33 is fixed and the analyzing crystal 34 is moved on a straight line passing the analytical point of the sample 33, and the position and direction of the X-ray detector 35 are simultaneously moved so that the sample 33, the analyzing crystal 34 and the X-ray detector 35 are always on the Rowland circle for measurement.

In order to allow the analyzing crystal 34 to make spectro-process without aberration, it is necessary to curve analyzing element into a cylindrical shape with a diameter of the Rowland circle being a radius. FIG. 7 shows an example of a conventional construction to bend the analyzing element. A pair of threaded constructions each comprising a motor 41 and a worm gear 37 causes supports 39 and 40 of a analyzing element 38 to advance and retreat from opposite sides to thereby change the curvature of the analyzing crystal 38.

Furthermore, as the X-ray detector 35, a proportional counter is ofter used, which is effective to detect a low energy X-ray. The proportional counter makes use of gas multiplication of gases filled in the counter, in which electrons of paired ions produced by the ionization function of the X-ray are accelerated under high voltage to produce an electron avalanche within the counter, thereby amplifying the number of the electrons to measure its charge as an electric pulse.

However, in the X-ray analytical apparatus comprised of the above-described conventional construction, it is necessary for scanning the wavelength to move the relative position between the sample, the analyzing crystal and the X-ray detector and the direction thereof while keeping them on the Rowland circle. This results in a uselessly larger size of the apparatus construction and makes it necessary to provide a drive mechanism capable of making a fine adjustment to keep a locating precision, and as a result, there gives rise to a problem in that the apparatus construction becomes complicated.

The construction to bend the analyzing element has a further problem in that a deviation in the moving direction tends to occur due to the precision in position of the supports and the precision in assembly of the drive mechanism, which leads to the difficulty of setting the curve radius with high precision; and that a displacement in the threaded portion caused by the motor leads to the change in curvature of the analyzing element, resulting in a difficulty of fine adjustment of the curve radius.

Furthermore, it is necessary to provide a slit in the X-ray detector in order to remove the scattered X-ray. In this case, there occurs a problem in that if a width of the slit is made narrower in order to improve the effect of the slit, a sensitivity of detection lowers so that the measuring time becomes uselessly long to lower the detection efficiency.

Moreover, in the case where the proportional counter is used as the X-ray detector, it is necessary to increase the gas multiplication rate for detecting the low energy X-ray. In such a case, higher voltage is applied to an anode wire. However, when the applied voltage is increased, the counter tends to deteriorate, thus spoiling the precision of measurement. Therefore, the voltage applied to the anode wire can be raised merely to an allowable limit, thus posing a problem in that a sufficient sensitivity for the detection of the low energy X-ray cannot be obtained.

It is therefore an object of the present invention to provide an X-ray analytical apparatus of a wavelength dispersion type using a microprobe of ion beam and applying an improvement in construction of essential parts for overcoming the problems as noted above with respect to prior art.

Furthermore, the conventional X-ray analysis by way of irradiation of ion beams has a problem in that since a measurement making use of a parallel beam is employed, an irradiation spot is wide such as a millimeter order, and as a result, a resolving power of wavelength degrades, failing to make the measurement with high accuracy. This poses a problem in that when the irradiation spot is controlled to be small by the slit, the sensitivity of the detection lowers and the measuring time becomes prolonged.

SUMMARY OF THE INVENTION

For improving the aforementioned problems, the present invention provides an X-ray analytical apparatus in which an irradiation point of a sample irradiated by an ion beam, a center at which a characteristic X-ray generated from said irradiation point is subjected to spectro-process by a analyzing element having a predetermined radius of curvature, and a measuring point for measuring a specific wavelength X-ray subjected to said spectro-process are arranged in the arrangement of a Rowland circle, said sample being irradiated by the ion beam, said specific wavelength X-ray being detected to make the analysis of the sample, said apparatus comprising ion beam scanning means for deflecting said ion beam to scan in a fine region of said sample; spectro-means comprising a curvature changing mechanism for changing a radius of curvature of said analyzing element and a rotational stage for rotating said analyzing element to adjust an incident angle of said characteristic X-ray; and X-ray detection means of a lengthy position sensitive type having an X-ray sensing region in a direction of changing an incident angle of said specific wavelength X-ray and measuring an incident position and strength of the X-ray.

The curvature changing mechanism is provided to regulate a pressure applied to a pressing member supported by a parallel spring construction which deforms merely in a pressing direction to thereby change the curvature of the analyzing element.

Furthermore, the X-ray detection means of a lengthy position sensitive type is constituted by a gas-flow type proportional counter, which is provided with means for regulating a gas pressure within the gas-flow type proportional counter.

According to the present invention, the ion beam is shaped into a microprobe, which is controlled to be deflected to scan in a fine region of a sample, a characteristic X-ray generated by irradiation of the ion beam is subjected to spectro-process by an analyzing element set to a predetermined radius of curvature by means of a curvature changing mechanism, and the X-ray having a specific wavelength selected by the spectro-process is detected by the position sensitive X-ray detection means. The ion beam irradiation point of the sample, the center of the analyzing element and the X-ray detection point of the X-ray detection means are arranged on the Rowland circle. When an angle of the analyzing element is set by the rotational stage to an incident angle of the specific X-ray determined by the detection element on the sample, a wide range of wavelengths can be spectro-measured while the sample, the analyzing element and the X-ray detection means remain fixed in position. That is, since the X-ray detection means is provided with a lengthy sensing portion, even if the incident position of the X-ray is changed, the measurement can be made while the position of the detector remains fixed. Being the position sensitive type detector, it is possible to collect incident position information of the X-ray different with wavelength. As a result, it is possible to measure the wavelength and strength of the X-ray while distinguishing each X-ray quantum.

Accordingly, it is not necessary to provide a slit in the X-ray detector according to the present invention.

In the above-described curvature changing mechanism, since a pressure is applied to a analyzing element through a parallel spring construction, it is possible to change the curvature under a reduced pressure caused by elastic deformation to render precise fine adjustment. Further, since a rigidity is exhibited with respect to a deformation other than the direction to bend the analyzing element cylindrically by means of the parallel spring, it is possible to set a precise radius of curvature. With this construction, it is possible to change the radius of curvature of the analyzing element according to the detection wavelength of the X-ray. Thus, it is not necessary to move the position of the analyzing element, and the analyzing measurement by way of the Rowland arrangement can be realized by a compact apparatus construction.

The X-ray detection means is constituted by the gas-flow type proportional counter, in which gas pressure within the counter can be regulated. It is therefore possible to select a gas pressure which is most effective for absorption of the X-ray according to the wavelength of the X-ray.

Accordingly, the anode voltage need not be regulated too high and a sufficient detection sensitivity can be obtained. Thus it is possible to maintain the performance of the counter for a long period of time.

As described above, according to the present invention, the ion beam is shaped into a microprobe, which is controlled to be deflected to scan in a fine region of a sample, a characteristic X-ray generated by irradiation of the ion beam is subjected to spectro-process by an analyzing element set to a predetermined radius of curvature by means of a curvature changing mechanism, and the X-ray having a specific wavelength selected by the spectro-process is detected by the position sensitive X-ray detection means.

The ion beam irradiation point of the sample, the center of the analyzing element and the X-ray detection point of the X-ray detection means are arranged on the Rowland circle. When an angle of the analyzing element is set by the rotational stage to an incident angle of the specific X-ray determined by the detection element on the sample, a wide range of wavelengths can be spectro-measured while the sample, the analyzing element and the X-ray detection means remain fixed in position. That is, since the X-ray detection means is provided with a lengthy sensing portion, even if the incident position of the X-ray is changed, the measurement can be made while the position of the detector remains fixed. Being the position sensitive type detector, it is possible to remove incident position information of the X-ray different with wavelength. Therefore, it is possible to measure the wavelength and strength of the X-ray while distinguishing each X-ray quantum.

Accordingly, it is not necessary to provide a slit in the X-ray detector according to the present invention.

In the above-described curvature changing mechanism, since a curve pressure is applied to a analyzing element through a parallel spring construction, it is possible to change the curvature under a reduced pressure caused by elastic deformation to render precise fine adjustment. Furthermore, since a rigidity is exhibited with respect to a deformation other than the curve direction to bend the analyzing element cylindrically by means of the parallel spring, it is possible to set a precise radius of curvature. With this construction, it is possible to change the radius of curvature of the analyzing element according to the detection wavelength of the X-ray. Thus, it is not necessary to move the position of the analyzing element, and the spectral measurement by way of the Rowland arrangement can be realized by a compact apparatus construction.

The X-ray detection means is constituted by the gas-flow type proportional counter, in which gas pressure within the counter can be regulated. It is therefore possible to select a gas pressure which is most effective for absorption of the X-ray according to the wavelength of the X-ray.

Accordingly, the anode voltage need not be regulated too high and a sufficient detection sensitivity can be obtained. Thus it is possible to maintain the performance of the counter for a long period of time, thus maintaining a highly reliable analytic result.

DESCRIPTION OF THE PREFERRED EMBODIMENTS

For better understanding of the present invention, the embodiments in which the present invention was embodied will be described hereinafter with reference to the accompanying drawings. The following embodiments are mere examples of the present invention and the technical scope of the present invention is not limited thereby.

Figure 1:
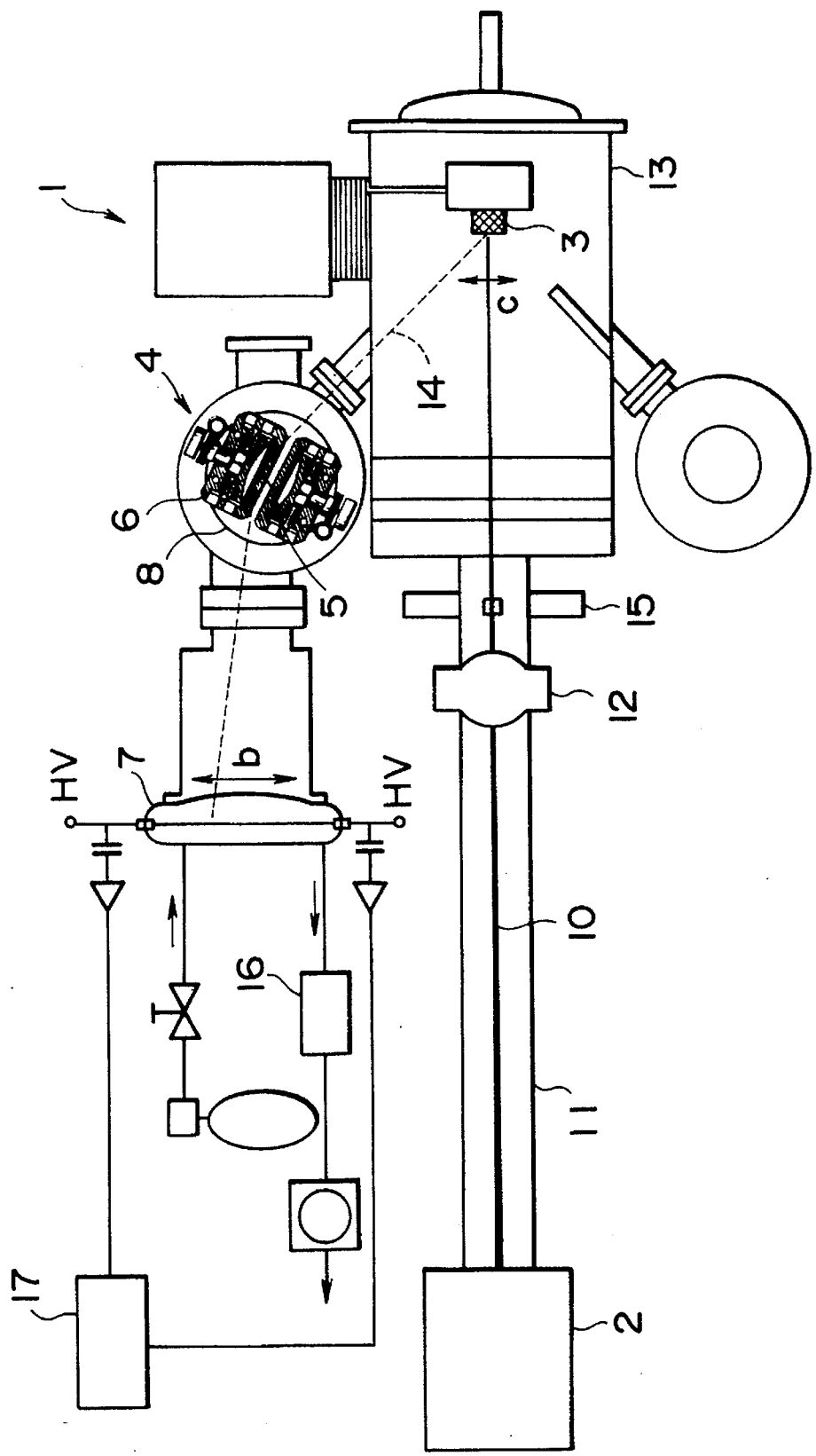
FIG. 1 is a schematic view showing the construction of an X-ray analytic apparatus according to an embodiment of the present invention.
Figure 2:
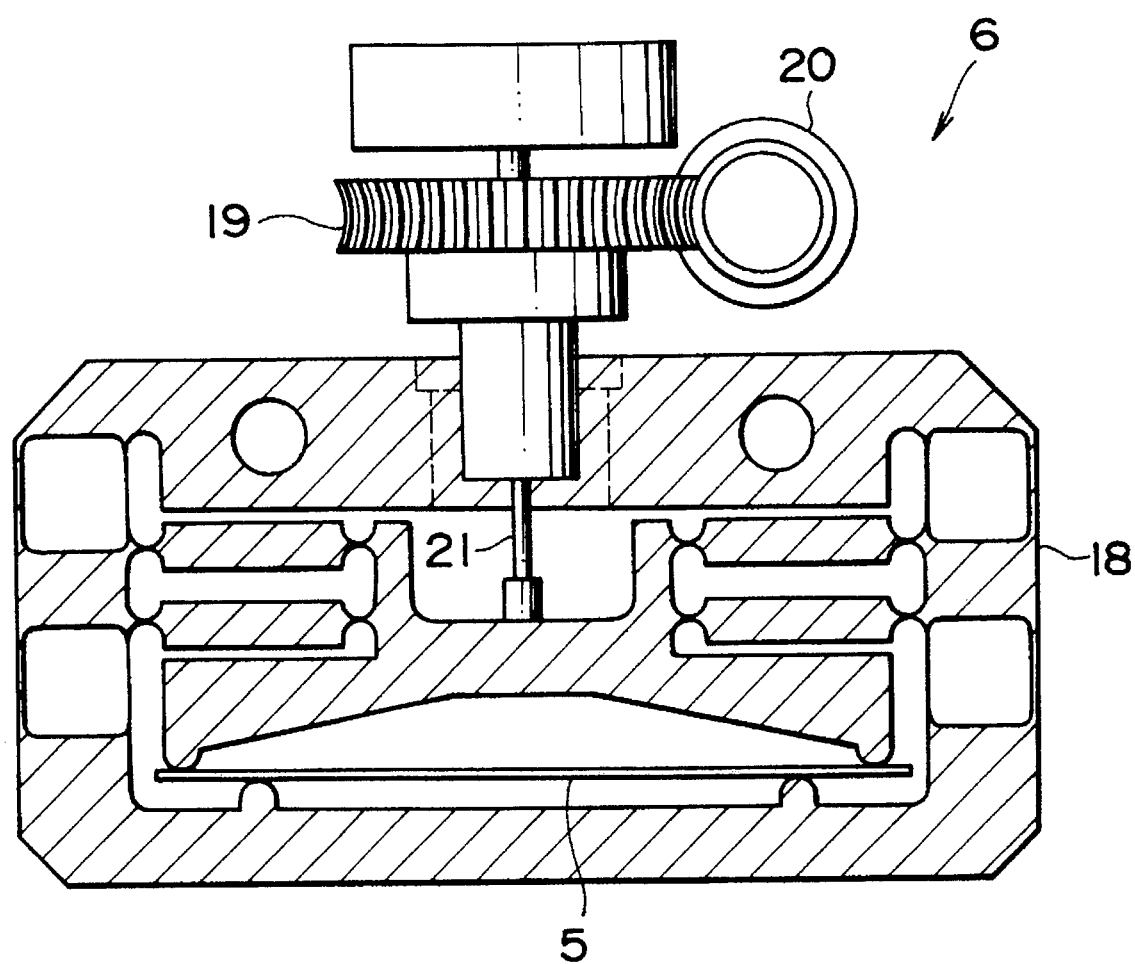
FIG. 2 is a side view showing the construction of a monolithic curvature changing mechanism according to an embodiment.
Figure 3:
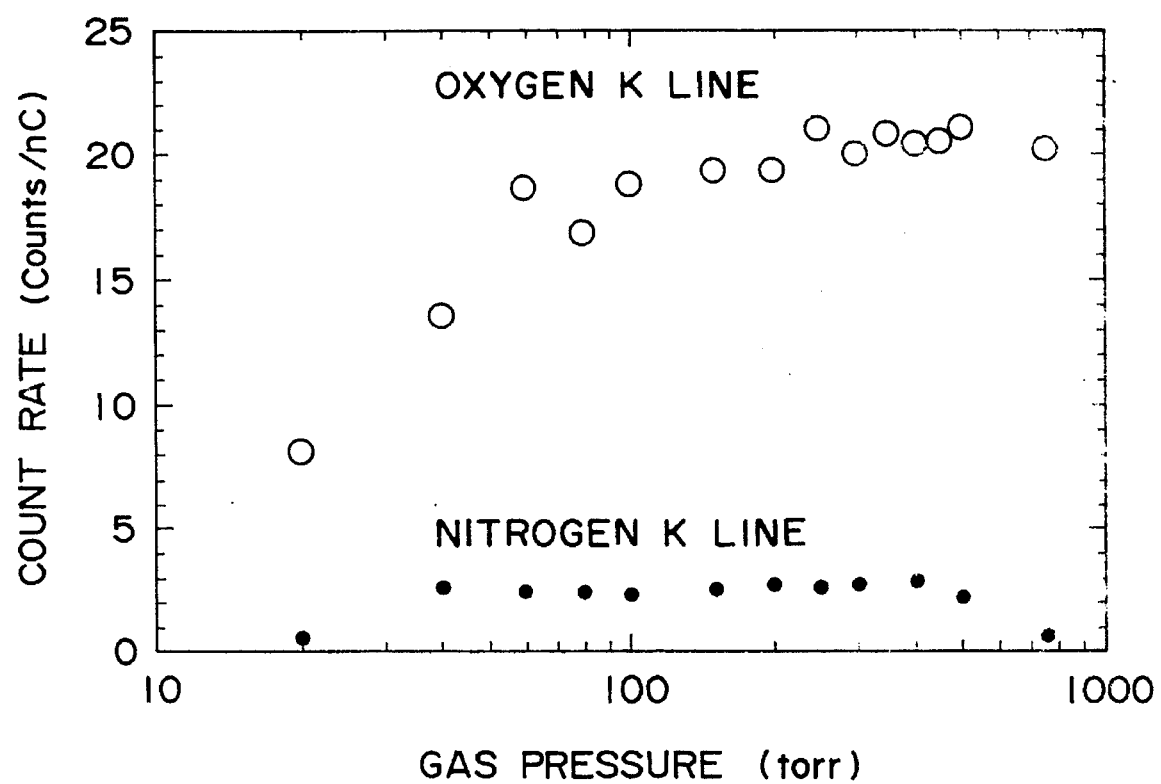
FIG. 3 is a graph showing the change in counts/nC on the basis of gas pressure of a proportional counter according to an embodiment.
Figure 4:
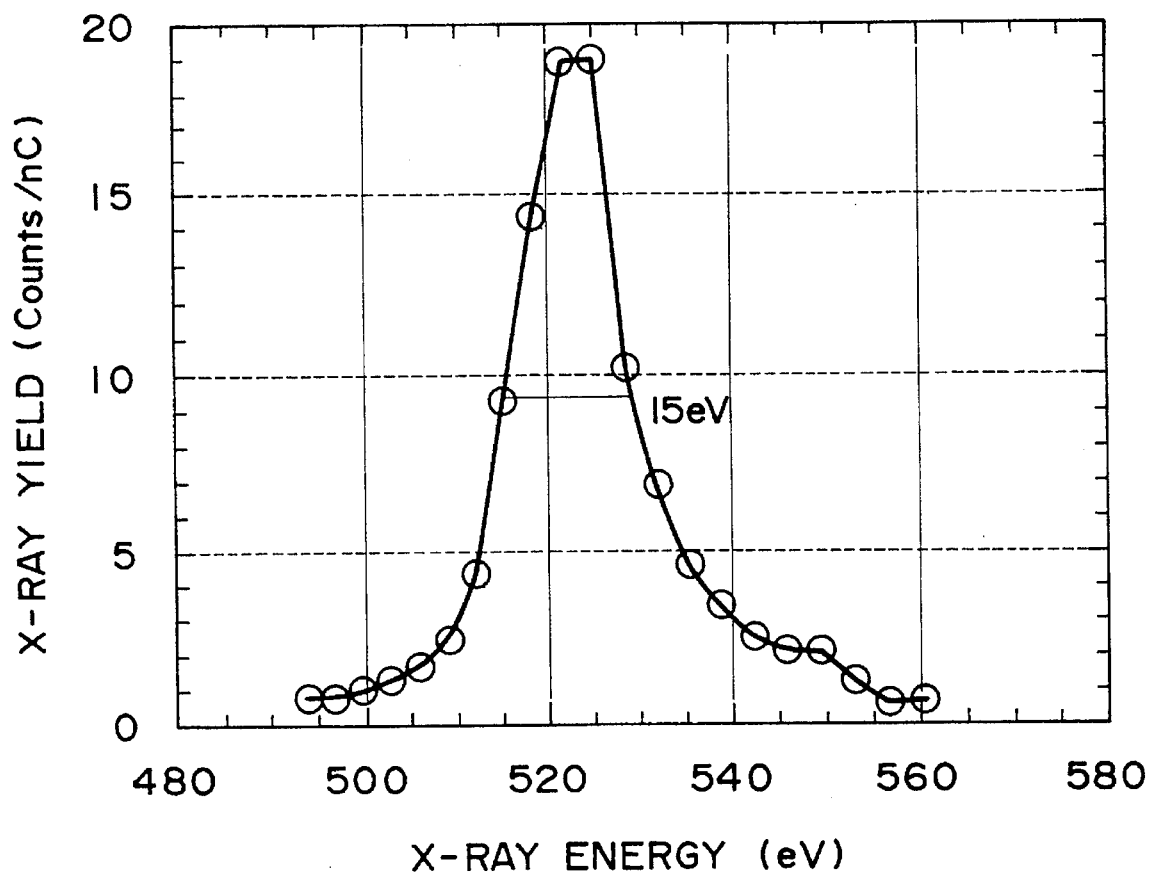
FIG. 4 is a graph showing the analyzing results of the characteristic X-ray of oxygen by the X-ray analytic apparatus according to an embodiment.
Figure 5:
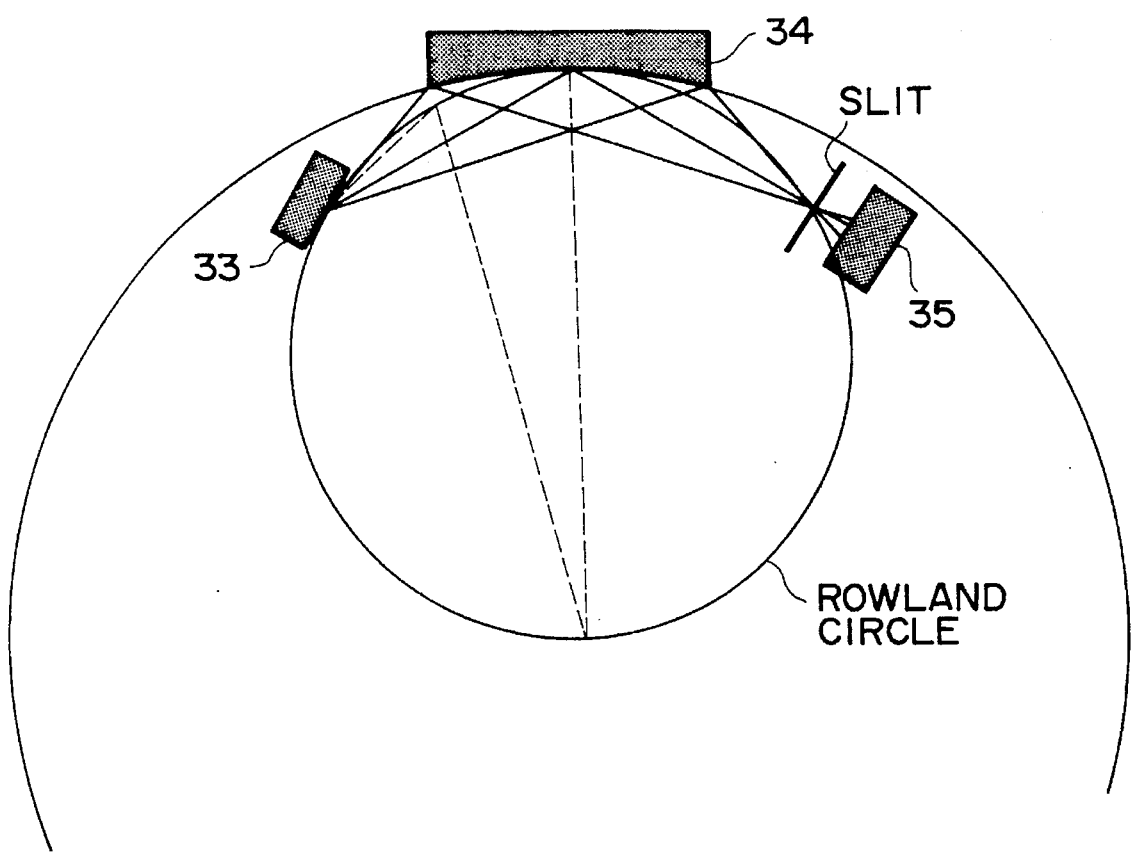
FIG. 5 is a schematic view showing the general construction of the X-ray analytic apparatus using a conventional curved crystal.
Figure 6:
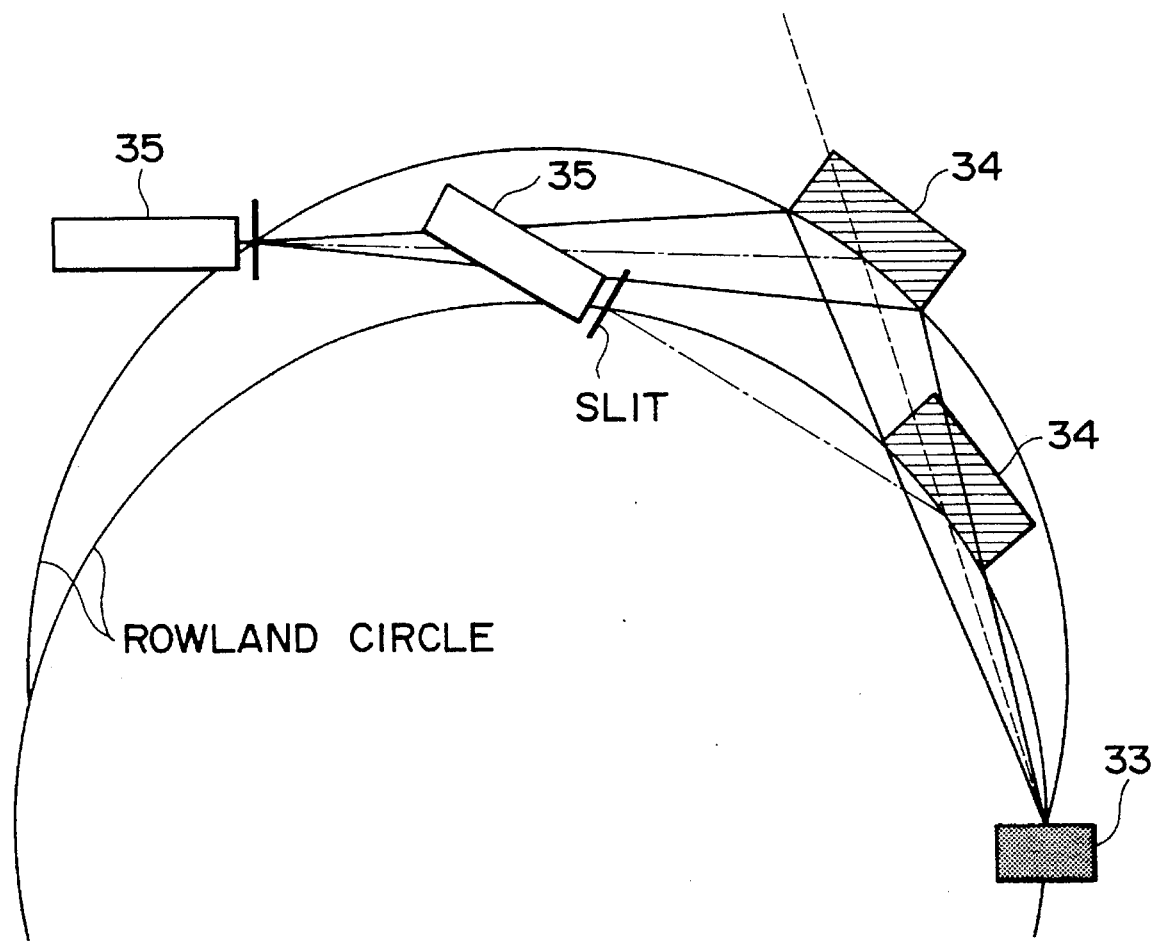
FIG. 6 is a schematic view showing the construction of the wavelength scanning by the conventional X-ray analytic apparatus.
Figure 7:
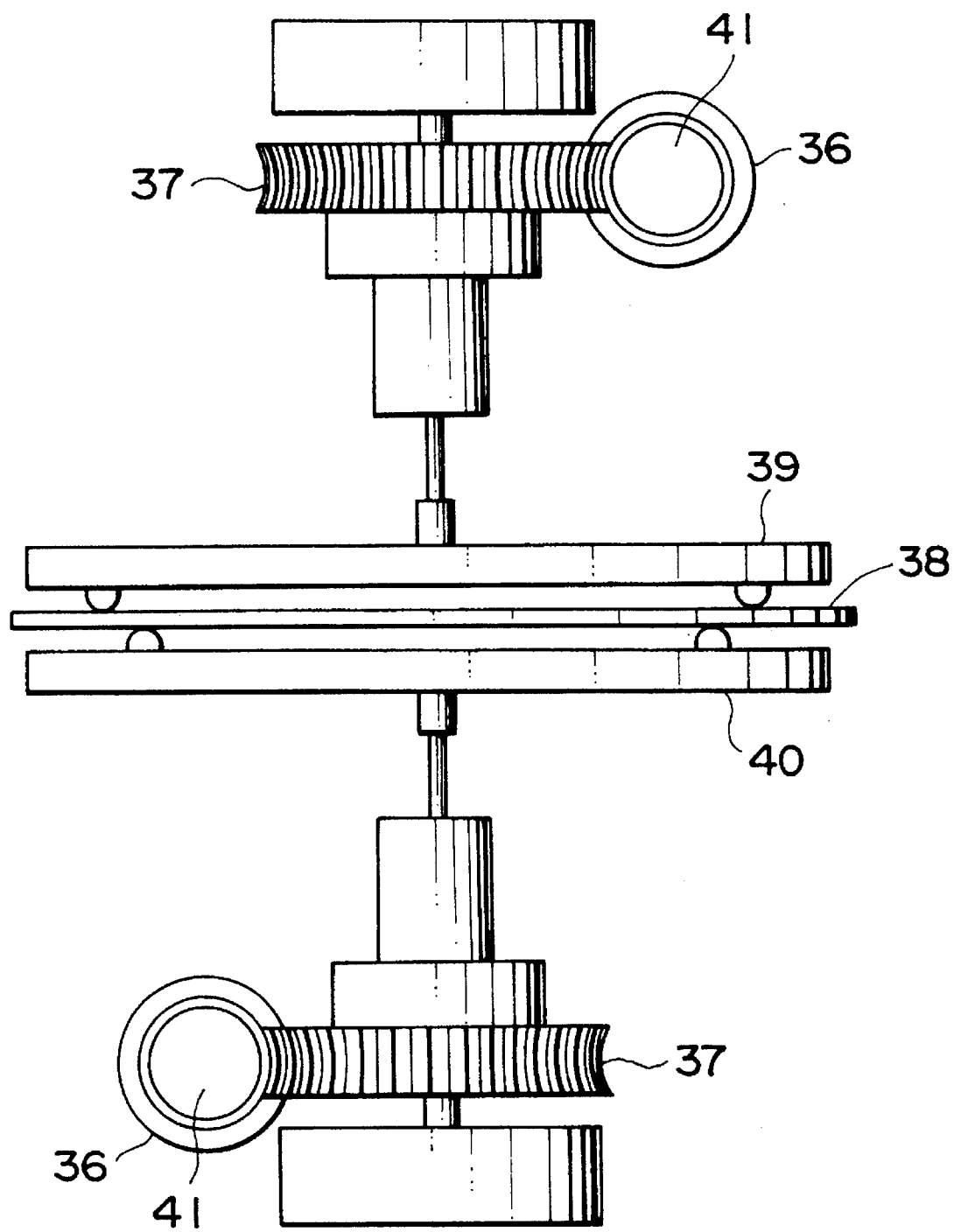
FIG. 7 is a side view showing the construction of the conventional curvature changing mechanism.

FIG. 1 is a schematic view showing the construction of a X-ray analytic apparatus according to one embodiment of the present invention; FIG. 2 is a sectional view showing the construction of a crystal curve mechanism according to an embodiment; FIG. 3 is a graph showing the change of counts/nC caused by a gas pressure of a proportional counter according to an embodiment; and FIG. 4 is a graph showing the spectral result of the characteristic X-ray of oxygen according to the X-ray analytic apparatus.

In FIG. 1, an X-ray analytic apparatus 1 according to an embodiment comprises ion beam scanning means comprising an ion beam generator 2, a magnetic lens 12 to make a microprobe and a deflector 15 for scanning a sample 3 by an ion beam, a vacuum vessel 13 having the sample 3 arranged at a predetermined position, an X-ray analyzing-unit (spectro-means) for subjecting a characteristic X-ray generated from the sample 3 irradiated by the ion beam to sepctro-process and condensation, and a proportional counter (X-ray detection means) for measuring wavelength and strength of the characteristic X-ray subjected to spectro-process.

In the above-described construction, a high energy ion beam 10 generated by the ion beam generator 2 is drawn in a direction of a vacuum duct 11. The ion beam 10 is shaped by a slit or an ion-kind selecting filter not shown and is converged by a magnetic lens 12. The converged beam is irradiated onto the sample 3 disposed within a vacuum vessel 13 provided with a load-lock mechanism with an irradiation spot having a size of micron. An electron of a constituent element in the range of beam irradiation is excited from the sample 3 irradiated by the ion beam 10 to generate a characteristic X-ray 14. The characteristic X-ray 14 is diffracted by the analyzing element 5 of the X-ray spectro-unit (spectro-means), and only the X-ray of wavelength λ given in Equation below is subjected to spectro-process by the interference effect.

$$2 \cdot d \cdot \sin \theta = n \cdot \lambda \quad (1)$$

wherein d is the grating constant in the case where the analyzing element 5 is of a crystal grating construction and the multilayer film period in the case where it is of a multilayer film; θ is the incident angle of X-ray 14 into the analyzing element 5; and n=1, 2, 3... are the order of diffraction, normally n=1 which is strongest in strength.

The analyzing element 5 is held by the curvature changing mechanism 6 for changing the radius of curvature of the element, the mechanism 6 being loaded on the rotational stage 8. The analyzing element 5 is curved by the curvature changing mechanism 6 with the radius of curvature 2·R given in the following Equation (2) corresponding to the spectral wavelength λ.

$$2 \cdot R \cdot \sin \theta = L \quad (2)$$

wherein R is the radius of a Rowland circle in which the irradiation point of ion beam of the sample 3, the center point of the analyzing element 5 and the X-ray measuring point (the condensed focal point by way of the analyzing element 5) caused by the proportional counter 7 are arranged; and L is the distance between the irradiation point of ion beam and the center point of the analyzing element 5, (the center point of the analyzing element and the X-ray measuring point). This distance is maintained constant irrespective of the spectral wavelength. The incident angle θ of the characteristic X-ray to the analyzing element 5 is adjusted by rotating the rotational stage 8 on which the curvature changing mechanism 6 is mounted. The curvature changing mechanism 6 and the rotational stage 8 are controlled to be driven by a controller not shown.

The curvature changing mechanism 6 is constituted as shown in FIG. 2. As shown in FIG. 2, the analyzing element 5 is held by a monolithic construction 18 having a composite parallel spring construction and formed integrally. A drive force of a motor 20 is applied to a center part of the composite parallel spring of the construction 18 through a worm gear 19 and a fine thread 21 to thereby curve and deform the analyzing element 5 through the composite parallel spring. Applied pressure to a center part of the construction is reduced by the spring and finally applied to the analyzing element 5. As a result a fine adjustment with high accuracy can be obtained. Furthermore, since the construction 18 exhibits a rigidity with respect to deformations other than the direction in which the analyzing element 5 is curved and deformed cylindrically, it is possible to set a radius of curvature with high accuracy.

The characteristic X-ray 14 subjected to spectro-process by the analyzing element 5 is measured in strength of X-ray and wavelength by the proportional counter 7. If the spectral wavelength is different, the trace of the characteristic X-ray 14 subjected to spectro-process changes so that the incident position moves in a direction of arrow b shown in FIG. 1. However, the proportional counter 7 according to the present embodiment is designed to enable correspondence to the entire incident direction in the length form as shown. The proportional counter 7 is in the form of a lengthy position sensitive proportional counter, and an anode wire is extended in correspondence to the lengthy X-ray incident window. The X-ray incident window is formed from a high polymer film having a thickness of 1 μm or less supported by a mesh support so as to obtain a detection sensitivity even with respect to the X-ray less than 1 keV. With the construction of the proportional counter 7, even if the incident position of the characteristic X-ray 14 is changed due to the spectral wavelength, it is possible to make measurement while the position of the detector remains fixed without the need of a complicated drive system for moving the position of the X-ray detector while maintaining the Rowland configuration as in the conventional construction. Accordingly, the whole construction is also compact.

The proportional counter 7 is of a gas flow type from a viewpoint of a limitation of airtightness of material for the X-ray incident window. A multiplication gas formed of a rare gas such as Ar, Ne or the like flows into the counter. It is necessary to maintain the pressure of the multiplication gas constant for the stability of the calculating efficiency and the amplifying rate. To this end, a pressure controller 16 is disposed above a gas pipe. Since the X-ray absorbing characteristic with respect to the gas pressure differs also with the wavelength of the X-ray, pressure is regulated also according to the wavelength to be measured so that the optimal absorption of X-ray occurs to amplify the gas. Accordingly, since the rate of gas multiplication is optimized every wavelength, measurement with superior S/N can be made in all the elements. Further, since it is not necessary to apply too high voltage to the anode wire, the performance can be maintained for a long period of time by application of voltage within a using limit, and a highly reliable analytic result can be always obtained.

FIG. 3 is a graph obtained by confirmation through the experiments of the optimized condition of the counts/nC by regulation of the gas pressure. In this example, an amplifying gas used comprises a mixed gas of 80% of Ar and 20% of methane. A glass plate is used for oxygen, and a baron nitride is used for nitrogen. The probe condition is that a hydrogen ion beam of energy 990 keV is converged into a beam irradiation size of 30 μm×50 μm for measurement. As shown in FIG. 3, it is understood that for both elements, the counts/nC in a certain range of pressure is maximum.

Further, the anode wire is fabricated so as to have a considerable resistance per length, and a collected charge is divided between two amplifiers connected at opposite ends of the anode wire in a proportion simply related to a position of mutual action. Accordingly, outputs of two amplifiers can be arithmetically processed by a signal processor 17 to thereby detect even a position at which the X-ray amplification on the anode wire occurs, that is, an incident position of the characteristic X-ray. With this function, each X-ray quantum discriminates the wavelength to count it, and therefore, the scattered X-ray can be removed without using a conventional slit.

The operation of the X-ray analysis using the X-ray analytical apparatus 1 constructed as described above will be described hereinafter.

For example, a crystal grating construction is employed as the analyzing element 5. The grating constant is 40 angstroms. In the case where detection of oxygen is carried out in connection with the sample 3, K emission line of oxygen is 23.62 angstroms, and when the spectral wavelength is determined, the incident angle θ to the analyzing element 5 is determined to be 17.2 degrees from Equation (1). In accordance with this result, the rotational stage 8 is driven to rotate the curvature changing mechanism 6 so that the incident angle of the characteristic X-ray 14 is θ=17.2 degrees. The fine adjustment of the incident angle θ is difficult to be realized merely by the operation of the rotational stage 8 because the accuracy of angle feed due to the characteristic of the drive motor is present. However, the rough setting will suffice and the range of wavelength in the vicinity of the incident angle set by scanning beam is continuously scanned. Therefore, the fine adjustment is not necessary and the apparatus can be constructed simply. The radius of curvature of the analyzing element 5 is curved with the radius of curvature 2.R given by Equation (2).

The measurement is made by deflecting the ion beam 10 by the deflector 15 in the direction of c shown in FIG. 1 and scanning a part to be analyzed of the sample 3. The incident angle of the characteristic X-ray to the analyzing element 5 with respect to the scanning range of the beam is continuously scanned in a certain range of angle about the incident angle set by the operation of the rotational stage. As a result, the measurement of spectra in the range of wavelength including the spectral wavelength λ is continuously made. FIG. 4 shows the analyzing result of the characteristic X-ray of oxygen, and it is understood that according to the apparatus, a resolving power of angle can be attained with sufficient accuracy.

What is claimed is:

1. An X-ray analytical apparatus in which an irradiation point of a sample irradiated by an ion beam, a spectral center at which a characteristic X-ray generated from said irradiation point is subjected to spectro-process by an analyzing element having an adjustable radius of curvature, and a measuring point for measuring a specific wavelength X-ray subjected to said spectro-process are arranged in the arrangement of a Rowland circle, said sample being irradiated by the ion beam, said specific wavelength X-ray being detected to make the analysis of the sample, said apparatus comprising:

ion beam scanning means for deflecting said ion beam to scan in a fine region of said sample;

spectro-means comprising a curvature changing mechanism for changing a radius of curvature of said analyzing element and a rotational stage for rotating said analyzing element to adjust an incident angle of said characteristic X-ray; and X-ray detection means of a lengthy position sensitive type having an X-ray sensing region in a direction of changing an incident angle of said specific wavelength X-ray and measuring an incident position and strength of the X-ray.

2. The X-ray analytical apparatus according to claim 1, wherein said curvature changing mechanism is provided to regulate a pressure applied to a pressing member supported by a monolithic parallel spring construction which deforms merely in a pressing direction to thereby change the radius of the curvature of the analyzing element.

3. The X-ray analytical apparatus according to claim 1, wherein said X-ray detection means of a lengthy position sensitive type is constituted by a gas-flow type proportional counter, which is provided with means for regulating a gas pressure within the gas-flow type proportional counter.

4. An X-ray analytical apparatus in which an irradiation point of a sample irradiated by an ion beam, a spectral center at which a characteristic X-ray generated from said irradiation point is subjected to spectro-process by an analyzing element having an adjustable radius of curvature, and a measuring point for measuring a specific wavelength X-ray subjected to said spectro-process are arranged in the arrangement of a Rowland circle, said sample being irradiated by the ion beam, said specific wavelength X-ray being detected to make the analysis of the sample, said apparatus comprising:

ion beam scanning means for deflecting said ion beam to scan in a fine region of said sample;

spectro-means comprising a curvature changing mechanism for changing said radius of curvature of said analyzing element and a rotational stage for rotating said analyzing element to adjust an incident angle of said characteristic X-ray into said analyzing element; and X-ray detection means of a lengthy position sensitive type having an X-ray sensing region in a direction of changing an incident angle of said specific wavelength X-ray and measuring an incident position and strength of the X-ray, said X-ray detection means being fixed in position relative to said irradiation point.

\* \* \* \* \*